United States Patent
El-Haddad et al.

(10) Patent No.: US 10,045,831 B2
(45) Date of Patent: Aug. 14, 2018

(54) INSTRUMENT TRACKING IN OCT-ASSISTED SURGERY

(71) Applicant: THE CLEVELAND CLINIC FOUNDATION, Cleveland, OH (US)

(72) Inventors: Mohamed T. El-Haddad, Cleveland, OH (US); Yuankai K. Tao, Shaker Heights, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 130 days.

(21) Appl. No.: 15/149,709

(22) Filed: May 9, 2016

(65) Prior Publication Data
US 2016/0324593 A1 Nov. 10, 2016

Related U.S. Application Data

(60) Provisional application No. 62/158,006, filed on May 7, 2015.

(51) Int. Cl.
*G01B 9/02* (2006.01)
*A61B 90/00* (2016.01)
(Continued)

(52) U.S. Cl.
CPC ............ *A61B 90/37* (2016.02); *A61B 3/0025* (2013.01); *A61B 3/102* (2013.01); *A61B 3/13* (2013.01);
(Continued)

(58) Field of Classification Search
CPC ......... A61B 90/37; A61B 90/20; A61B 34/20; A61B 3/102; A61B 3/13; A61B 3/0025;
(Continued)

(56) References Cited

U.S. PATENT DOCUMENTS

2003/0218755 A1* 11/2003 Wei .................. A61B 3/102
356/497
2012/0184846 A1 7/2012 Izatt et al.
(Continued)

OTHER PUBLICATIONS

Berthold, Karsten, et al. "Simultaneous Stereo-Optical Navigation of Medical Instruments for Brachytherapy." 4th European Conference of the International Federation for Medical and Biological Engineering. Springer Berlin Heidelberg, 2009.
(Continued)

*Primary Examiner* — Hwa Lee
(74) *Attorney, Agent, or Firm* — Tarolli, Sundheim, Covell & Tummino LLP

(57) ABSTRACT

Systems and methods are provided for a microscope-integrated intraoperative scanner system having automated tracking of an instrument tip. A scanning mirror is configured such that a field of view of the OCT system is determined by a position or orientation of the scanning mirror. A drive system is configured to control the scanning mirror. Camera assemblies are configured to determine respective two-dimensional projections of the positions of markers attached to a surgical instrument. A stereo vision system is configured to determine a three-dimensional location of each of the markers from the determined two-dimensional positions. An instrument tracking component is configured to determine a position of a working tip of the surgical instrument according to the determined three-dimensional locations. A drive control is configured to instruct the drive system to adjust the scanner mirror to control the field of view of the OCT system.

13 Claims, 3 Drawing Sheets

(51) Int. Cl.
| | |
|---|---|
| H04N 13/02 | (2006.01) |
| G06T 7/00 | (2017.01) |
| G02B 21/00 | (2006.01) |
| A61B 3/13 | (2006.01) |
| A61B 3/10 | (2006.01) |
| G02B 26/10 | (2006.01) |
| A61B 3/00 | (2006.01) |
| A61B 34/20 | (2016.01) |
| A61B 90/20 | (2016.01) |
| G06T 7/73 | (2017.01) |

(52) U.S. Cl.
CPC .............. *A61B 34/20* (2016.02); *A61B 90/20* (2016.02); *G02B 21/0012* (2013.01); *G02B 26/105* (2013.01); *G06T 7/0012* (2013.01); *G06T 7/73* (2017.01); *H04N 13/0239* (2013.01); *A61B 2090/3735* (2016.02); *G01B 9/02091* (2013.01); *G06T 2207/10028* (2013.01); *G06T 2207/10101* (2013.01); *G06T 2207/30204* (2013.01)

(58) Field of Classification Search
CPC ........ A61B 2090/3735; H04N 13/0239; G02B 26/105; G02B 21/0012; G01B 9/02091; G06T 2207/30204; G06T 2207/10101; G06T 2207/10028; G06T 7/73; G06T 7/0012
See application file for complete search history.

(56) References Cited

U.S. PATENT DOCUMENTS

2013/0060146 A1  3/2013  Yang et al.
2014/0221822 A1  8/2014  Ehlers et al.

OTHER PUBLICATIONS

Hahn, Paul, et al. "The use of optical coherence tomography in intraoperative ophthalmic imaging." Ophthalmic Surgery, Lasers and Imaging Retina 42.4 (2011): S85-S94.

Oberkampf, Denis, Daniel F. DeMenthon, and Larry S. Davis. "Iterative pose estimation using coplanar points." Computer Vision and Pattern Recognition, 1993. Proceedings CVPR'93., 1993 IEEE Computer Society Conference on. IEEE, 1993.

Petersen, Thomas. "A comparison of 2D-3D pose estimation methods." Aalborg University—Institute for Media Technology Computer vision and graphics. Aalborg University (2008).

Ren, Jian, et al. "Manual-scanning optical coherence tomography probe based on position tracking." Optics letters 34.21 (2009): 3400-3402.

Stoyanov, Danail. "Surgical vision." Annals of biomedical engineering 40.2 (2012): 332-345.

Tao, Yuankai K., et al. "Intraoperative spectral domain optical coherence tomography for vitreoretinal surgery." Optics letters 35.20 (2010): 3315-3317.

West, Jay B., and Calvin R. Maurer. "Designing optically tracked instruments for image-guided surgery." IEEE transactions on medical imaging 23.5 (2004): 533-545.

Zhang, Zhengyou. "A flexible new technique for camera calibration." IEEE Transactions on pattern analysis and machine intelligence 22.11 (2000): 1330-1334.

PCT International Search Report and Written Opinion for PCT/US2016/031452, dated Aug. 12, 2016, pp. 1-10.

* cited by examiner

INSTRUMENT TRACKING IN OCT-ASSISTED SURGERY

RELATED APPLICATIONS

This application claims priority from U.S. patent application Ser. No. 62/158,006, filed 7 May 2015, which is incorporated herein in its entirety.

TECHNICAL FIELD

This invention relates to medical systems, and more particularly, to instrument tracking in OCT-assisted surgery.

BACKGROUND

Retinal Optical Coherence Tomography (OCT) allows the visualization of high-resolution cross-sectional images of tissue microstructure and is the gold-standard for ophthalmic diagnosis. Recently, intraoperative OCT has been used perioperatively to image pre- and post-operative manipulations to verify the completion of surgical goals and aid clinical decision-making. However, perioperative imaging requires interruption of surgery and precludes real-time surgical guidance. This limitation was overcome by the recent development of microscope-integrated intraoperative OCT systems (iOCT), which allows live cross-sectional imaging concurrent with surgery. A major limitation to the clinical utility of intraoperative imaging is real-time visualization of instrument-tissue interactions. In iOCT, visualization of surgical maneuvers may be performed by spatial compounding under the guidance of a Heads-Up Display (HUD) unit. Volumetric scans around the instrument tip are sparsely sampled and spatially compounded across the instrument's cross-section to visualize instrument-tissue interactions. However, spatial compounding inherently trades-off temporal resolution and field-of-view (FOV), which generally limits video-rate visualization to the tip of surgical instruments. Another limitation of spatial compounding is the OCT FOV needs to be precisely aligned with the surgical instrument and along its projected axis of motion.

SUMMARY OF THE INVENTION

In accordance with an aspect of the present invention, a microscope-integrated intraoperative optical coherence tomography (OCT) scanner system having automated tracking of an instrument tip is provided. At least one scanning mirror is configured such that a field of view of the OCT scanner system is determined by at least one of a position and an orientation of the at least one scanning mirror. A drive system is configured to control the at least one of the position and the orientation of the at least one scanning mirror. A plurality of camera assemblies are configured to determine respective two-dimensional projections of the positions of a plurality of markers attached to a surgical instrument. A stereo vision system is configured to determine a three-dimensional location of each of the plurality of markers from the determined two-dimensional positions at the plurality of camera assemblies. An instrument tracking component is configured to determine a position of a working tip of the surgical instrument according to the determined three-dimensional locations of the plurality of markers. A drive control is configured to instruct the drive system to adjust the at least one of the position and the orientation of the at least one scanner mirror such that the field of view of the OCT scanner system is determined from a position of the working tip of the surgical instrument.

In accordance with another aspect of the present invention, a method is provided for adjusting a field of view of microscope-integrated intraoperative optical coherence tomography (OCT) scanner system to track the tip of a surgical instrument. Respective two-dimensional projections of the positions of a plurality of markers attached to a surgical instrument is determined. A three-dimensional location of each of the plurality of markers is determined from the determined two-dimensional positions at the plurality of camera assemblies and a known relationship among the plurality of camera assemblies. A position of a working tip of the surgical instrument is determined according to the determined three-dimensional locations of the plurality of markers. At least one of the position and the orientation of at least one scanner mirror associated with the OCT scanner system are controlled such that the field of view of the OCT scanner system is dependent on the position of the working tip of the surgical instrument.

In accordance with yet another aspect of the present invention, a method is provided for adjusting a field of view of microscope-integrated intraoperative optical coherence tomography (OCT) scanner system to track the tip of a surgical instrument, the method. A model comprising a plurality of markers in a known arrangement is moved within a field of view of a plurality of camera assemblies. A plurality of images of the model are captured at each of the plurality of camera assemblies, such that each camera generates a plural set of two-dimensional locations for each marker. A relative pose between the plurality of camera assemblies is determined from the plural set of two-dimensional locations for each marker at each of the plurality of cameras and the known arrangement of the plurality of markers. Respective two-dimensional projections of the positions of a plurality of markers attached to a surgical instrument are determined. A three-dimensional location of each of the plurality of markers is determined from the determined two-dimensional positions at the plurality of camera assemblies and the relative pose. A position of a working tip of the surgical instrument is determined according to the determined three-dimensional locations of the plurality of markers. At least one of the position and the orientation of at least one scanner mirror associated with the OCT scanner system is controlled such that the field of view of the OCT scanner system is determined by the position of the working tip of the surgical instrument.

DETAILED DESCRIPTION

In accordance with an aspect of the present invention, systems and methods are provided for tracking an instrument tip and adjusting a field of view of an optical coherence tomography (OCT) system to follow the instrument tip. In one implementation, a stereo-vision system, comprising two or more cameras tracking a set of active or passive markers, are used to determine multiple positions on or near a free tip of the instrument and, from this information, determine a position of the working tip of the instrument. The position and/or orientations of a set of scanning mirrors associated with the OCT scanner can be altered to maintain the working tip of the instrument within the field of view of the OCT scanner.

Figure 1:
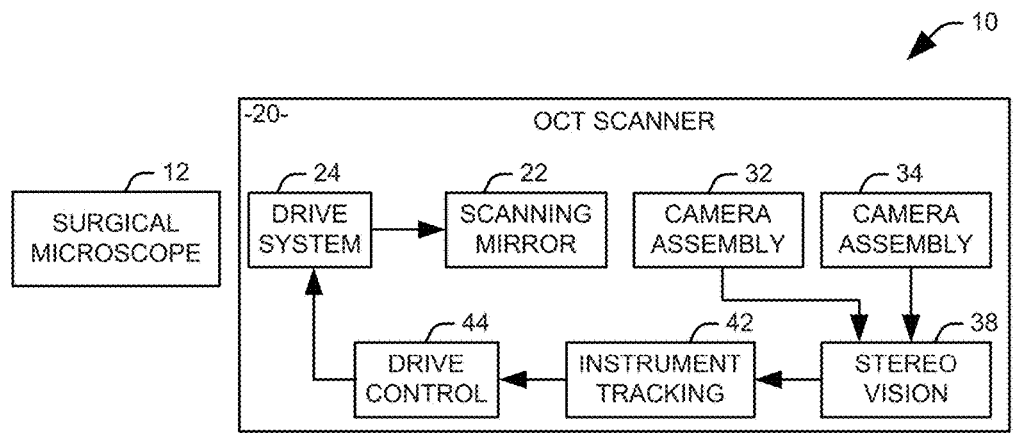
FIG. 1 illustrates a microscope-integrated intraoperative optical coherence tomography scanner system having automated tracking of an instrument tip during a surgical procedure.

To this end, FIG. 1 illustrates a microscope-integrated intraoperative optical coherence tomography (OCT) scanner system 10 having automated tracking of an instrument tip during a surgical procedure. The scanner system 10 includes a surgical microscope 12, and an OCT scanning unit 20 configured to image a target location in conjunction with at least one optical component associated with the surgical microscope 12, such as an objective lens.

The OCT scanning unit 20 includes at least one scanning mirror 22 configured such that a field of view of the OCT scanner system is determined by at least one of a position and an orientation of the at least one scanning mirror. A drive system 24 configured to control the at least one of the position and the orientation of the at least one scanning mirror. Current generation tabletop and microscope-integrated OCT systems utilize actuating mirrors for two-dimensional lateral scanning of their imaging beam. In combination with the axial sectioning capabilities of OCT, this yields three-dimensional tomograms of the tissues of interest. These actuating mirrors are generally paired galvanometer scanners, but may consist of resonant scanners and MEMS scanners or a combination thereof. To reduce system complexity, conventional OCT systems position paired scanners in close proximity, but do not optically image the angular scan fields between the mirror faces to the back aperture of their imaging objective or pupil plane.

A plurality of camera assemblies 32 and 33 configured to determine respective two-dimensional projections of the positions of a plurality of markers attached to a surgical instrument. The camera assemblies 32 and 33 can include appropriate filters to limit the response of the camera assemblies to a band of wavelengths within one of the infrared, ultraviolet, or visible range, depending on the wavelength of emission or reflection associated with the plurality of markers. It will be appreciated that, in the illustrated implementation 10, two camera assemblies 32 and 33 are shown, but in practice, additional cameras may be employed to improve the accuracy of the location of the working tip of the instrument. It will be appreciated that the markers can be active, that is, light emitting, or passive, that is, light reflecting. Where passive markers are used, the system 10 can include an appropriate light source (not shown).

Depth resolution in stereo vision, $\Delta z$, is directly proportional to the square of the imaging distance, z, and inversely proportional to both the focal length of and separation distance between the cameras, conventionally defined as the baseline. For a fixed imaging distance and focal length, the baseline can be maximized in order to achieve optimal depth resolution. It will be appreciated, however, that available baseline in an intraoperative imaging system can be limited, and in one implementation, the upper limit of the baseline was set to one hundred millimeters as not exceed the body width of the intraoperative OCT system. The cameras were pointed inwards in a converging stereo setup with a tilt that maximized the stereo vision FOV overlap at a desired imaging distance of approximately nineteen centimeters. This imaging distance was set by the axial distance between the bottom of the intraoperative OCT chassis and ophthalmic surgical microscope focal plane.

The outputs of the plurality of camera assemblies are provide to a stereo vision system 38 configured to determine a three-dimensional location of each of the plurality of markers from the determined two-dimensional positions at the plurality of camera assemblies. Essentially, the stereo vision system 38 triangulates for the 3-D position of a point in space based on the disparity in its projection in the image planes of the plurality of camera assemblies. Assuming proper calibration, the three-dimensional position of the markers relative to one camera can be determined and then transformed, if needed, to a global coordinate system associated with the system 10.

An instrument tracking component 42 is configured to determine a position of a working tip of the surgical instrument according to the determined three-dimensional locations of the plurality of markers. In one implementation, two or more markers are placed along an axis of the surgical instrument, such that an orientation and position of the instrument can be determined, and a position of the working tip can be determined from the determined orientation and position of the instrument and known properties of the instrument. In another implementation, two or more markers are placed along an axis of the surgical instrument and another marker is placed on a opposite side of the instrument from the two or more markers to allow for the determination to better account for the deviation of the markers from the centerline of the instrument.

A drive control 44 is configured to instruct the drive system to adjust the at least one of the position and the orientation of the at least one scanner mirror 22 such that the field of view of the OCT scanner system 20 is determined by the position of the working tip of the surgical instrument. To this end, the position of the working tip of the surgical instrument can be transformed from a coordinate system associated with the stereo vision system to a coordinate system associated with the OCT scanner system 20 via an appropriate coordinate transform. In one implementation, the drive system 24 is instructed to adjust the at least one scanner mirror 22 such that the OCT field of view remains centered on the working tip of the instrument. In another implementation, the drive system 24 is instructed to adjust the at least one scanner mirror 22 such that the OCT field of view remains at a predetermined displacement from the position of the working tip. Accordingly, the surgical procedure can be performed without the need to continuously reposition the field of view of the OCT scanner.

Figure 2:
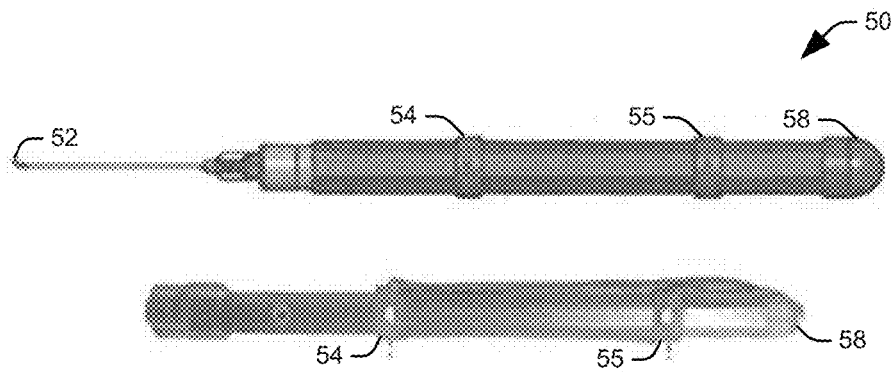
FIG. 2 illustrates one example of a surgical instrument having a working tip and a plurality of markers and illustrated in two opposing views.

FIG. 2 illustrates one example of a surgical instrument 50 having a working tip 52 and a plurality of markers 54, 55, and 58 and illustrated in two opposing views. In the illustrated implementation, each of the plurality of markers 54, 55, and 58 include light emitting diodes (LED) and configured to emit light at a wavelength of around nine hundred forty nanometers with a one hundred and sixty degree beam angle. Two axial markers 54 and 55 also include collars for affixing the LEDs to the instrument and an off-axis marker 58 is attached to a cap placed on a free end of the instrument. The two axial markers 54 and 55 were radially offset from the axis of the instrument, and the off-axis marker 58 is used to compensate for the thickness of the instrument at each axial marker position.

Figure 3:
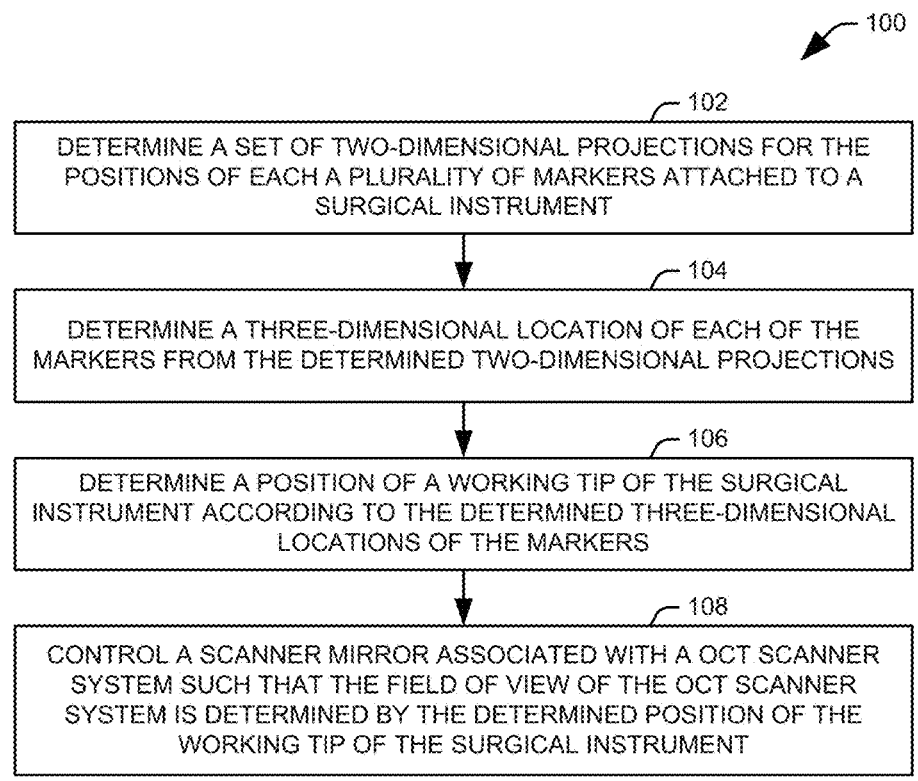
FIG. 3 illustrates one example of a method for adjusting a field of view of microscope-integrated intraoperative optical coherence tomography (OCT) scanner system to track the tip of a surgical instrument.
Figure 4:
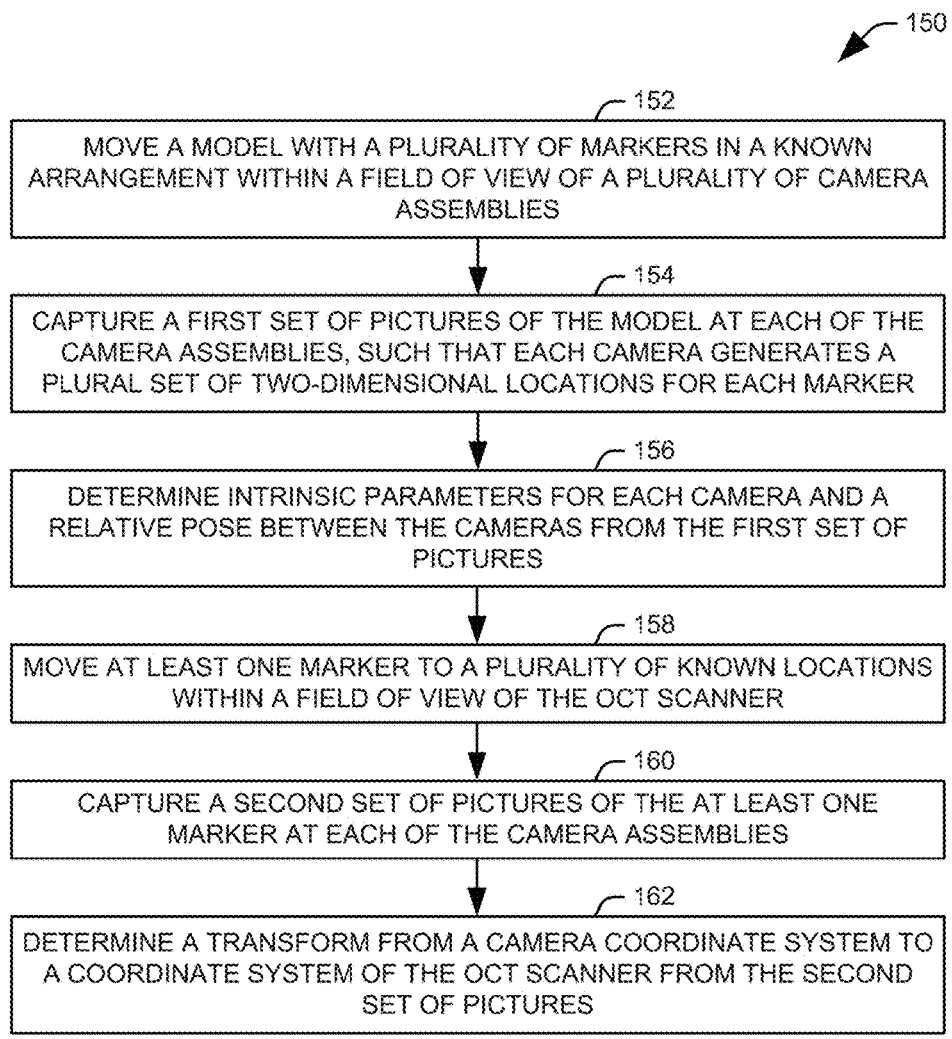
FIG. 4 illustrates a method for calibrating a stereo vision system for instrument tracking in a microscope-integrated intraoperative optical coherence tomography (OCT) scanner system.

In view of the foregoing structural and functional features described above in FIGS. 1 and 2, example methodologies will be better appreciated with reference to FIGS. 3 and 4. While, for purposes of simplicity of explanation, the methodologies of FIGS. 3 and 4 are shown and described as executing serially, it is to be understood and appreciated that the present invention is not limited by the illustrated order, as some actions could in other examples occur in different orders and/or concurrently from that shown and described herein.

FIG. 3 illustrates one example of a method 100 for adjusting a field of view of microscope-integrated intraoperative optical coherence tomography (OCT) scanner system to track the tip of a surgical instrument. At 102, respective two-dimensional projections of the positions of a plurality of markers attached to a surgical instrument are determined at each of a plurality of camera assemblies. For example, the markers can emit or reflect light of a particular wavelength, and the cameras can be fitted with appropriate filters to detect light only around that particular wavelength, with the location of each marker within the camera coordinate system representing the two-dimensional projection of the marker position.

At 104, a three-dimensional location of each of the plurality of markers is determined from the determined two-dimensional positions at the plurality of camera assemblies. Using a known relationship among the cameras, reflected as calibration parameters, such as a relative pose between two cameras, the determined two-dimensional positions can be used to determine a point in three-dimensional space within a coordinate domain associated with one of the cameras. In an example two cameras, giving three dimensional locations represented as vectors $m_{left}$ and $m_{right}$, the three dimensional position (X, Y, Z) can be determined in a coordinate frame of the right camera from the calibration parameters, such that:

$$\begin{bmatrix} Z_{right} \\ Z_{left} \end{bmatrix} = ([-Rm_{right}m_{left}]^T[-Rm_{right}m_{left}])^{-1}[-Rm_{right}m_{left}]^T t \quad \text{Eq. 1}$$

$$Y = \frac{S_y Y}{Z_{right}} + y_0 \quad \text{Eq. 2}$$

$$X = \frac{S_x X}{Z_{right}} + \frac{S_y Y \tan\theta}{Z_{right}} + x_0 \quad \text{Eq. 3}$$

where $S_X$ is a scaling parameter based on pixel length for the right camera in a x direction, $S_y$ is a scaling parameter based on pixel length for the right camera in a y direction, θ is a skew angle of a given pixel in the right camera, and ($x_0$, $y_0$) represent the pixel coordinates of the right camera origin, R is a rotation matrix relating the coordinate systems of the two cameras, and t is a translation vector relating the coordinate systems of the two cameras.

At 106, a position of a working tip of the surgical instrument is determined according to the determined three-dimensional locations of the plurality of markers. In one implementation, to calculate the working-tip position, a directional vector is defined by two markers positioned to be parallel to a longitudinal instrument axis. The tip was then defined as a point along a vector parallel to the directional vector that intersected the location of a marker on a free tip of the instrument, for example, from a known length of the instrument. The two body markers were radially offset from the axis of the instrument and a marker at the free-tip of the instrument is used to compensate for the thickness of the instrument at each axial marker position. Instrument orientation was defined as the angle between the directional vector and the y-axis of the OCT coordinate system. A triangulation position error of each active marker and a desired orientation resolution determines a separation distance between the body markers. For example, for a desired orientation resolution of 0.9° and a triangulation position error of 150 μm, the axial markers should be separated by 19.1 mm. In practice, a value 2.5 times that can be used to account for addition error sources, such as variability in the placement of the markers and ensure significant orientation resolution.

At 108, controlling at least one of the position and the orientation of at least one scanner mirror associated with the OCT scanner system such that the field of view of the OCT scanner system is determined by the position of the working tip of the surgical instrument. For example, the field of view can be centered on the working tip or slightly displaced from the working tip. An orientation of the field of view can also be controlled according to the instrument position, such that sequential B-scans are aligned parallel and perpendicular to the instrument axis. Each determined position is transformed into the OCT coordinate system, and the scanner mirror or mirrors are controlled to maintain the position and orientation of the OCT scanner system field of view.

To maintain an OCT agnostic platform, conventional sawtooth scanner drive waveforms, generated from an iOCT system, are relayed through a data acquisition board to add voltage and phase offsets calculated from the stereo vision system to track the tip position and orientation of surgical instruments. At the beginning of each imaging session, one second of the drive signal for each galvanometer was sampled at 100 KS/s on two analog channels and stored in internal buffers. The zero-crossings in the stored sampled signals were determined to identify the start of each scan trajectory. For each channel. the corresponding output buffer outputs contiguous chunks of samples from the stored drive signal corresponding to a single B-scan. The output buffer looped over the stored signal circularly, starting and ending at a zero crossing to avoid discontinuities in the output signal. The modified output signals were then output to their respective galvanometer scanner drivers to maintain the desired position and orientation of the OCT field of view.

FIG. 4 illustrates a method 150 for calibrating a stereo vision system for instrument tracking in a microscope-integrated intraoperative optical coherence tomography (OCT) scanner system. As discussed previously, using either of a pair of stereo vision cameras as a reference frame, the 3-D coordinates of point M relative to that camera can be calculated using similar triangles. This process, however, assumes a perfectly parallel pair of cameras and ignores the contribution of the image sensor in the image projection. In the practical case, there will be an arbitrary rotation and translation between the cameras, referred to as the relative pose, and the contribution of the image sensor for each camera, the intrinsic parameters, that needs to be accounted for.

To this end, at 152 a model, comprising a plurality of markers in a known arrangement, is moved to a plurality of locations within a field of view of a plurality of camera assemblies. In one implementation, the model comprises four markers forming four corners of a square having a side length of 17.5 millimeters. At 154, a plurality of images of the model are captured at each of the plurality of camera assemblies, such that each camera generates a plural set of two-dimensional locations for each marker.

At 156, intrinsic parameters for each of the camera assemblies and a relative pose between the camera assemblies are determined from the plural set of two-dimensional locations for each marker. To this end, a homography matrix, H, is generated for each camera as:

$$H = A[Rt] \qquad \text{Eq. 1}$$

where A represents the intrinsic parameters matrix, and [Rt] is a 3×4 matrix that describes the rotation and translation between the cameras. For a reference camera, [R t] will become an identity matrix.

The intrinsic parameters describe the properties of the image sensor that depend mainly on the shape of its pixels, and the pixel coordinates that represent the origin, which is not necessarily at the center of the sensor. For a given camera, the intrinsic parameters matrix can be represented as:

$$H = \begin{bmatrix} S_x & (\tan\theta)S_y & x_0 \\ 0 & S_y & y_0 \\ 0 & 0 & 1 \end{bmatrix} \qquad \text{Eq. 2}$$

where $S_x$ is a scaling parameter based on pixel length in a x direction, $S_y$ is a scaling parameter based on pixel length in a y direction, $\theta$ is a skew angle of a given pixel in the camera, and ($x_0$, $y_0$) represent the pixel coordinates of the camera origin.

Once the homography matrix for each camera has been determined, a second calibration step is performed to determine a transform from a coordinate domain associated with the reference camera to a coordinate system associated with the OCT scanner system. A model, including at least one marker, is moved within the field of view of the OCT scanner system and the plurality of cameras at 158. It will be appreciated that this can be the same model as that used in 152, or a different model. In one implementation, this can be done with a surgical instrument appropriately affixed with markers, such as the instrument illustrated in FIG. 2. In one implementation, the model is moved to four known positions in the OCT coordinate system, with two lying on an x-axis of the OCT coordinate system and two lying on a y-axis of the coordinate system. At 160, a plurality of images of the model are captured at each of the plurality of camera assemblies.

At 162, the transform from the coordinate domain associated with the reference camera to the coordinate system associated with the OCT scanner system is determined from the plurality of images of the model captured at 160. The coordinate transformation is implemented as a three-dimensional translation and rotation. In one implementation, the three-dimensional position of the marker or markers can be determined from the captured images and arranged as a 3×M matrix, $X_{stereo}$, in which each of M determined positions are stored as ordered triplets representing coordinates in the camera reference plane. $X_{motor}$ is a 3×M matrix representing the position of the model within the OCT coordinate frame. From this data, a 3×3 rotation matrix, R, is determined such that:

$$X_{motor} = R \times X_{stereo} \qquad \text{Eq. 3}$$

An appropriate optimization algorithm, such as least squares optimization, can be used to solve for the rotation matrix R.

Even cameras of the same model from the same manufacturer can have significant variation in their intrinsic parameters, leading to inaccurate positions for the instrument tip in the absence of such calibration. It will be appreciated that the calibration procedure of FIG. 4 allows for a significant increase in the accuracy of the system, which is allows for the submillimeter precision necessary for OCT assisted surgery.

Figure 5:
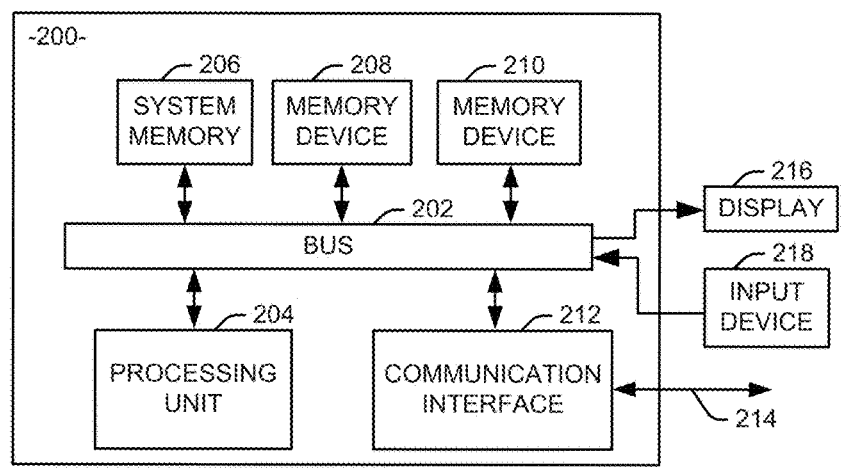
FIG. 5 is a schematic block diagram illustrating an exemplary system of hardware components capable of implementing examples of the systems and methods disclosed in FIGS. 1-4.

FIG. 5 is a schematic block diagram illustrating an exemplary system 200 of hardware components capable of implementing examples of the systems and methods disclosed in FIGS. 1-4, such as the stereo vision system 38, the instrument tracking component 42, and the drive control illustrated in FIG. 1. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a therapeutic delivery system in accordance with the present invention. Computer executable logic for implementing the diagnostic system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution, and can, in practice, refer to multiple, operatively connected apparatuses for storing machine executable instructions.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A microscope-integrated intraoperative optical coherence tomography (OCT) scanner system having automated tracking of an instrument tip, the system comprising:
   at least one scanning mirror configured such that a field of view of the OCT scanner system is determined by at least one of a position and an orientation of the at least one scanning mirror;
   a drive system configured to control the at least one of the position and the orientation of the at least one scanning mirror;
   a plurality of camera assemblies configured to determine respective two-dimensional projections of the positions of a plurality of markers attached to a surgical instrument;
   a stereo vision system configured to determine a three-dimensional location of each of the plurality of markers from the determined two-dimensional positions at the plurality of camera assemblies;
   an instrument tracking component configured to determine a position of a working tip of the surgical instrument according to the determined three-dimensional locations of the plurality of markers; and
   a drive control configured to instruct the drive system to adjust the at least one of the position and the orientation of the at least one scanner mirror such that the field of view of the OCT scanner system is determined from a position of the working tip of the surgical instrument;
   wherein the stereo vision system is configured to calculate a first ray from an origin of a first camera of the plurality of camera assemblies to a given one of the plurality of markers, calculate a second ray from a center point of a second camera of the plurality of camera assemblies to the given one of the plurality of markers, find a shortest line segment connecting the first ray and the second ray, and determining the three-dimensional location of the given one of the plurality of markers as a midpoint of the shortest line segment connecting the first ray and the second ray.

2. The microscope-integrated intraoperative OCT scanner system of claim 1, wherein each of the plurality of cameras are within one hundred millimeters of one another.

3. The microscope-integrated intraoperative OCT scanner system of claim 1, wherein at least a subset of the plurality of markers are aligned along a longitudinal axis of the surgical instrument and instrument tracking component is configured to determine an orientation of the instrument from the position of the plurality of markers.

4. The microscope-integrated intraoperative OCT scanner system of claim 3, wherein the surgical instrument comprises at least two of the plurality of markers aligned along a line parallel with a longitudinal axis of the surgical instrument and at least one marker of the plurality of markers that is not aligned along the line parallel with a longitudinal axis of the surgical instrument.

5. The microscope-integrated intraoperative OCT scanner system of claim 1, wherein the instrument tracking component is configured to transform the position of a working tip of the surgical instrument from a coordinate system associated with the stereo vision system to a coordinate system associated with the OCT scanner system via an appropriate coordinate transform.

6. The microscope-integrated intraoperative OCT scanner system of claim 1, wherein the markers are active markers implemented as infrared light emitting diodes.

7. The microscope-integrated intraoperative OCT scanner system of claim 1, wherein the drive control is configured to instruct the drive system to adjust the at least one of the position and the orientation of the at least one scanner mirror such that the field of view of the OCT scanner system is oriented perpendicular to an axis of the surgical instrument.

8. A method for adjusting a field of view of microscope-integrated intraoperative optical coherence tomography (OCT) scanner system to track the tip of a surgical instrument, the method comprising:
   determining respective two-dimensional projections of the positions of a plurality of markers attached to a surgical instrument;
   determining a three-dimensional location of each of the plurality of markers from the determined two-dimensional positions at the plurality of camera assemblies and a known relationship among the plurality of camera assemblies;
   determining a position of a working tip of the surgical instrument according to the determined three-dimensional locations of the plurality of markers;
   controlling at least one of the position and the orientation of at least one scanner mirror associated with the OCT scanner system such that the field of view of the OCT scanner system is determined by the position of the working tip of the surgical instrument;
   moving a model comprising a plurality of markers in a known arrangement within a field of view of the plurality of camera assemblies;
   capturing a plurality of images of the model at each of the first and second camera assemblies, such that each camera generates a plural set of two-dimensional locations for each marker;
   determining at least a portion of the known relationship among the plurality of camera assemblies as a relative pose from the plural set of two-dimensional locations for each marker at each of the first and second cameras and the known arrangement of the plurality of markers;
   moving a marker to a plurality of known locations within a field of view of the OCT scanner system;
   capturing a set of images of the marker at each of the plurality of camera assemblies; and
   determining the coordinate transform from the sets of images captured at each of the plurality of camera assemblies;
   recording each of the known locations within the coordinate system associated with the OCT scanner system as three-dimensional locations in a first matrix, $X_{motor}$;
   determining three-dimensional locations of the marker in the coordinate system associated with the plurality of camera assemblies as a second matrix, $X_{stereo}$; and
   solving the relationship $X_{motor} = R \times X_{stereo}$ for the coordinate transform, R, using an appropriate optimization algorithm.

9. The method of claim 8, wherein controlling at least one of the position and the orientation of at least one scanner mirror comprises controlling at least one of the position and the orientation of at least one scanner mirror associated with the OCT scanner system instruct the drive system to adjust the at least one of the position and the orientation of the at least one scanner mirror such that the field of view of the OCT scanner system is oriented perpendicular to an axis of the surgical instrument.

10. The method of claim 8, further comprising transforming the position of a working tip of the surgical instrument from a coordinate system associated with the stereo vision system to a coordinate system associated with the OCT scanner system via an appropriate coordinate transform.

11. The method of claim 8, wherein the markers are active markers implemented as infrared light emitting diodes.

12. The method of claim 8, further comprising transforming the position of the working tip of the surgical instrument from a coordinate system associated with the plurality of camera assemblies to a coordinate system associated with the OCT scanner system via a coordinate transform.

13. A method for adjusting a field of view of microscope-integrated intraoperative optical coherence tomography (OCT) scanner system to track the tip of a surgical instrument, the method comprising:
    moving a model comprising a plurality of markers in a known arrangement within a field of view of a plurality of camera assemblies;
    capturing a plurality of images of the model at each of the plurality of camera assemblies, such that each camera generates a plural set of two-dimensional locations for each marker;
    determining a relative pose between the plurality of camera assemblies from the plural set of two-dimensional locations for each marker at each of the plurality of cameras and the known arrangement of the plurality of markers;
    determining respective two-dimensional projections of the positions of a plurality of markers attached to a surgical instrument;
    determining a three-dimensional location of each of the plurality of markers from the determined two-dimensional positions at the plurality of camera assemblies and the relative pose;
    determining a position of a working tip of the surgical instrument according to the determined three-dimensional locations of the plurality of markers;
    transforming the position of the working tip of the surgical instrument from a coordinate system associated with the plurality of camera assemblies to a coordinate system associated with the OCT scanner system via a coordinate transform;
    controlling at least one of the position and the orientation of at least one scanner mirror associated with the OCT scanner system such that the field of view of the OCT scanner system is determined by the position of the working tip of the surgical instrument;
    moving a marker to a plurality of known locations within a field of view of the OCT scanner system;
    capturing a set of images of the marker at each of the plurality of camera assemblies; and
    determining the coordinate transform from the sets of images captured at each of the plurality of camera assemblies;
    recording each of the known locations within the coordinate system associated with the OCT scanner system as three-dimensional locations in a first matrix, $X_{motor}$;
    determining three-dimensional locations of the marker in the coordinate system associated with the plurality of camera assemblies as a second matrix, $X_{stereo}$; and
    solving the relationship $X_{motor} = R \times X_{stereo}$ for the coordinate transform, R, using an appropriate optimization algorithm.

* * * * *